US00PP16521P3

(12) United States Plant Patent
Redman

(10) Patent No.: US PP16,521 P3
(45) Date of Patent: May 9, 2006

(54) ***CHRYSANTHEMUM* PLANT NAMED 'GRACE TIME SALMON IMPROVED'**

(50) Latin Name: *Chrysanthemum morifolium*
Varietal Denomination: Grace Time Salmon Improved

(75) Inventor: Ruth Redman, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 94 days.

(21) Appl. No.: 10/993,262

(22) Filed: Nov. 18, 2004

(65) Prior Publication Data

US 2005/0114964 P1 May 26, 2005

Related U.S. Application Data

(60) Provisional application No. 60/524,739, filed on Nov. 20, 2003.

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

PP14,262 P2 11/2003 Boeder ..... Plt./286

OTHER PUBLICATIONS

Co–pending plant patent application Ser. No. 10/993,261 for the variety 'Grace Time Pink'.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *chrysanthemum* plant named 'Grace Time Salmon Improved,' having a good uniform canopy of salmon quill single flowers with a light green disc. The new variety has a medium vigor and a uniform spreading habit with a good foliage presentation.

1 Drawing Sheet

Latin name of the genus and species: Botanical classification: *Chrysanthemum morifolium.*

Variety denomination: The new *Chrysanthemum* variety denomination is 'Grace Time Salmon Improved.'

BACKGROUND OF THE INVENTION

The present invention comprises a new and distinct variety of *Chrysanthemums* botanically known as *Chrysanthemum morifolium,* and referred to by the variety name 'Grace Time Salmon Improved'.

'Grace Time Salmon Improved', identified as 20911-27, was discovered as a whole plant mutation found in a controlled cultivated planting of the variety 'Grace Time Pink' (U.S. Plant patent application Ser. No. 60/524,339). The new variety 'Grace Time Salmon Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Grace Time Salmon Improved' is a pot type of *Chrysanthemum* plant variety having salmon single quill type flowers with a light green disc.

Comparison with Parent

Plants of the new *Chrysanthemum* variety 'Grace Time Salmon Improved' are similar to the parent 'Grace Time Pink' in plant habitat and growth rate. In side-by-side comparisons in Chichester, West Sussex, United Kingdom, under commercial practice, plants of the new *Chrysanthemum* variety 'Grace Time Salmon Improved' compared to plants of the parent 'Grace Time Pink' in the following characteristics.

1. The new variety 'Grace Time Salmon Improved' produces salmon quill single flowers whereas the parent variety 'Grace Time Pink' produces purple single quill flowers.
2. Plants of the new variety 'Grace Time Salmon Improved' have a similar inflorescence to the plants of the parent variety 'Grace Time Pink.'

Comparison with Other Varieties

Plants of the new *Chrysanthemum* variety 'Grace Time Salmon Improved' are dissimilar to the variety, 'Mogul Time' (U.S. Plant Pat. No. 14,262) in plant habitat and growth rate. However, in side-by-side comparisons in Chichester, West Sussex, United Kingdom, under commercial practice, plants of the new *Chrysanthemum* variety 'Grace Time Salmon Improved' differed from plants of the variety 'Mogul Time' in the following characteristics.

1. The new variety 'Grace Time Salmon Improved' produces salmon quill single flowers whereas 'Mogul Time' produces purple quill spoon tip single flowers.
2. Plants of the new variety 'Grace Time Salmon Improved' have smaller and shorter inflorescence than plants of 'Mogul Time.'

BRIEF DESCRIPTION OF ILLUSTRATION

Typical specimens of the plant and flowers for the new *Chrysanthemum* variety 'Grace Time Salmon Improved' are shown in the accompanying digital photograph. The colors shown are as true as possible within the usual limits of this kind of illustration.

FIG. 1 is a whole plant view of the new variety 'Grace Time Salmon Improved' grown in a pot. The plant shown in the illustration is 56 days from the commencement of Short Days.

DETAILED BOTANICAL DESCRIPTION

The following description of the new *Chrysanthemum* variety 'Grace Time Salmon Improved' is of plants grown in a greenhouse in Chichester, West Sussex, United Kingdom in the month of September. The variety has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gm per liter. To produce a commercial product the plants may be pinched once with the center bud removed. The typical container size for commercial growth in 1 liter. It has been observed that the shelf life of the new variety is about 21 days with a response time of about 7.5 weeks. The new variety is suitable for growth in a temperature range of 15° C. to 25° C.

The new variety may be produced as a spray. The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright and free branching.
Height: 22 cm.
Width: 32 cm.
Stem:
- *Length* (*cm*).—5.
- *Diameter* (*cm*).—0.8.
- *Texture.*—Slightly pubescent.
- *Color.*—139C.

Branching characteristics: Upright and free branching.
Lateral branches:
- *Length* (*cm*).—14.
- *Diameter* (*cm*).—0.6.
- *Texture.*—Slightly pubescent.

Number of breaks from pinch: 5 to 7.
Response time: 52 days.
Vigor: Medium.
Shelf life: 21 days.
Life of blooms: 21 days.
Disease (susceptibility or resistance): None observed.
Pest (susceptibility or resistance): None observed.
Drought or temperature (susceptibility or resistance): None observed.
Growth retardant type and treatment: 3 applications of 2.5 gm/liter B9 @ 2, 21 and 28 days after sticking of unrooted cuttings.
The plants were grown for 2 weeks in Long Day conditions (20 hours of light) and then transferred to Short Day conditions (13 hours of dark).

Propagation:
- *Type.*—Vegetative Propagation via Stem Cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 8 to 12.
Compound or single: Single.
Arrangement of leaves: Alternate.
- *Shape of leaf.*—Typically 5 lobed.
- *Size of leaf.*—Width (cm): 4.5 Length (cm): 9.
- *Leaf apex.*—Acute.
- *Base.*—Obtuse.
- *Attachment.*—Petioled.
- *Aspect.*—Slightly Undulating.
- *Margin.*—Palmately lobed.
- *Surface characteristics.*—Top: Slightly Pubescent. Bottom: Pubescent.

Petiole:
- *Color.*—139B.
- *Length* (*cm*).—1.3.
- *Diameter* (*cm*).—0.2.

Venation:
- *Color.*—Upper side: 138B. Under side: 138C.

Color:
- *Mature leaf, upper side.*—Near 137C; under side: near 138A.
- *Young leaf, upper side.*—Near 137A; under side: near 138A.

Flower

Flower appearance: Matte.
Flower type: Single quill.
Flower form: Slightly cupped.
Flower shape: Circular.
Flowering habit: Cyme.
Number of blossoms per branch: 5.
Typical and observed flowering season: January to December.
Inflorescence form: Cyme.
- *Depth of fully expanded blossoms.*—1.5 cm.
- *Diameter of fully expanded blossoms.*—5 cm.

Phyllaries:
- *Number.*—18.
- *Color.*—138A.
- *Length.*—0.7 cm.
- *Width.*—0.2 cm.
- *Texture/appearance.*—Pubescent.

Peduncle:
- *Length* (*cm*).—13.
- *Diameter* (*cm*).—0.5.
- *Angle from stem* (*degrees*).—10.
- *Color.*—138B.
- *Surface.*—Pubescent.
- *Habit.*—Slightly undulating.
- *Strength.*—Strong.

Pedicel:
- *Length.*—Terminal: 3 cm; lateral: 4 cm.
- *Diameter* (*cm*).—0.2.
- *Color.*—138B.
- *Surface.*—Pubescent.
- *Habit.*—Slightly undulating.
- *Strength.*—Medium.

Ray florets:
*Form/shape.*—Straight and cylindrical.
*Texture/appearance.*—Matte.
*Number per flower.*—40.
*Length* (*cm*).—2.5 Width (cm): 0.4.
*Apex.*—Rounded.
*Base.*—Tapered.
*Margin.*—Entire.
Disc florets:
*Form/shape.*—Cylindric.
*Texture/appearance.*—Shiny.
*Number per flower.*—192.
*Length* (*cm*).—0.5; Width (cm): 0.1.
*Diameter of disc* (*cm*).—1.2.
Fragrance: None observed.
Flower bud (at onset of color):
*Length.*—1 cm.
*Diameter.*—0.7 cm.
*Form/shape.*—Globular.
General flower color:
1. *Ray florets, upper side.*—Immature: near 50A and 36B. Mature: near 50B and 36B. Older/Fading: near 50C and 36B.
2. *Ray florets, under side.*—Immature: near 56C. Mature: near 56C. Older/Fading: near 56D.
3. *Disc florets.*—Immature: near 151A. Mature: near 151B. Older/Fading: near 151B.
4. *Bud.*—50A.

Flower progression with age: There is no change with the flower form, but there is a slight color fading with age.

Reproductive Organs

Gynoecium present on Ray and Disc florets.
Ray florets per individual flower: Pistillate.
*Pistil number.*—40.
*Stigma color.*—154A.
*Stigma shape.*—Forked.
*Style color.*—154B.
*Style length* (*cm*).—0.3.
Disc florets per individual flower: Pistillate.
*Pistil number.*—90.
*Stigma color.*—154A.
*Stigma shape.*—Forked.
*Style color.*—154B.
*Style length* (*cm*).—0.3.
Androecium: None observed.
Fruit and seeds: None observed.

What is claimed is:

1. A new and distinct variety of *Chrysanthemum* plant, substantially as described and illustrated herein.

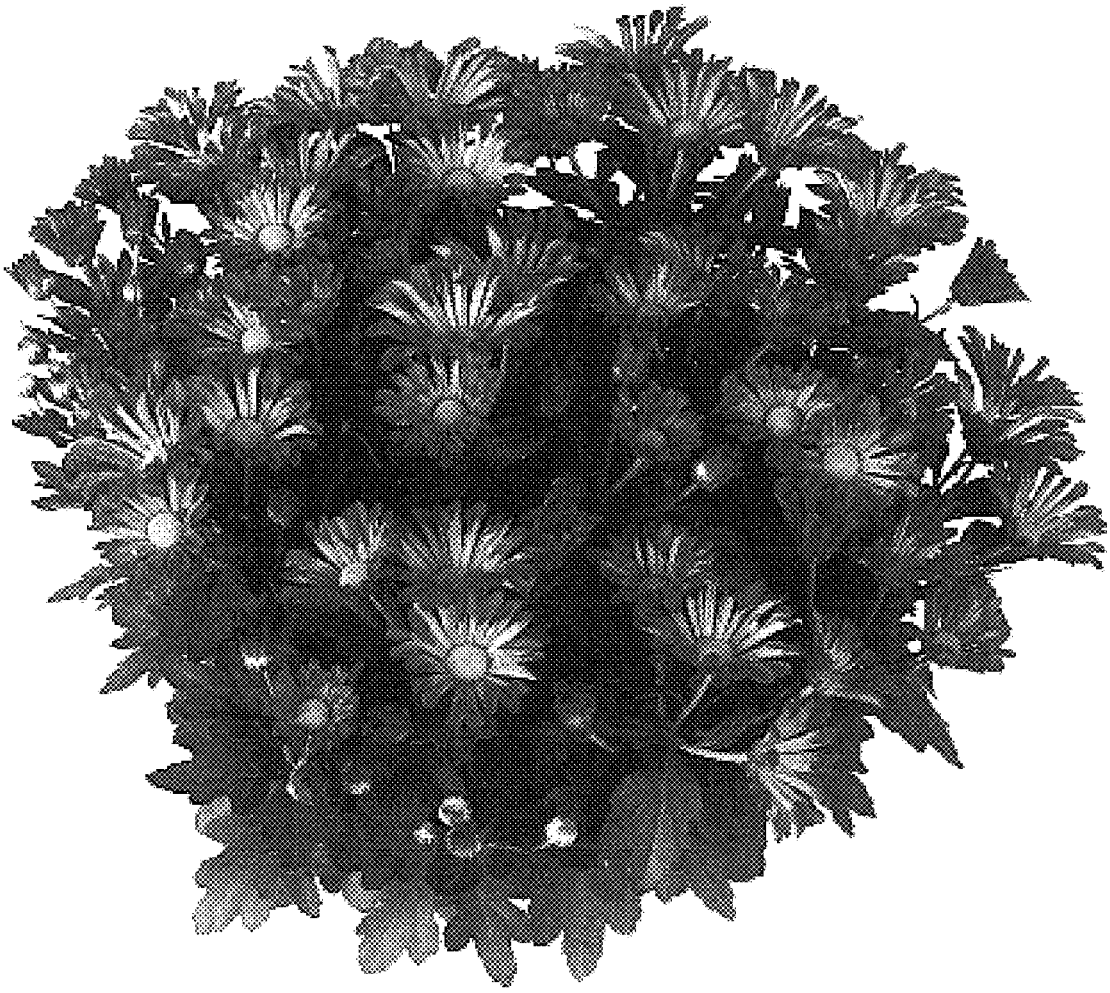

* * * * *